(12) United States Patent
Vahlberg et al.

(10) Patent No.: US 9,618,482 B2
(45) Date of Patent: Apr. 11, 2017

(54) DEVICE AND METHOD FOR REMOTELY DETERMINING THE IMPULSE RESPONSE OF AN OBJECT USING ELECTROMAGNETIC RADIATION

(71) Applicant: Totalförsvarets forskningsinstitut (FOI), Linköping (SE)

(72) Inventors: Claes Vahlberg, Linköping (SE); Joakim Vikström, Linköping (SE)

(73) Assignee: TOTALFORSVARETS FORSKNINGSINSTITUT (FOI), Linkoping (SE)

( * ) Notice: Subject to any disclaimer, the term of this patent is extended or adjusted under 35 U.S.C. 154(b) by 198 days.

(21) Appl. No.: 14/430,482

(22) PCT Filed: Sep. 23, 2013

(86) PCT No.: PCT/SE2013/051105
§ 371 (c)(1),
(2) Date: Mar. 23, 2015

(87) PCT Pub. No.: WO2014/046607
PCT Pub. Date: Mar. 27, 2014

(65) Prior Publication Data
US 2015/0253291 A1    Sep. 10, 2015

(30) Foreign Application Priority Data

Sep. 24, 2012   (SE) ..................................... 1251075

(51) Int. Cl.
*G01N 29/04*    (2006.01)
*G01N 29/44*    (2006.01)
(Continued)

(52) U.S. Cl.
CPC ........... *G01N 29/2418* (2013.01); *G01H 9/00* (2013.01); *G01N 29/04* (2013.01); *G01N 29/44* (2013.01);
(Continued)

(58) Field of Classification Search
CPC .... G01N 29/2418; G01N 29/04; G01N 29/44; G01N 2291/0289; G01N 2291/023
(Continued)

(56) References Cited

U.S. PATENT DOCUMENTS 3,946,388 A * 3/1976 Schifrine ................ G01S 7/04
342/113
5,955,669 A   9/1999 Egami
(Continued)

FOREIGN PATENT DOCUMENTS

CA   2785688   9/2011
DE   4004228   8/1991
(Continued)

OTHER PUBLICATIONS

Extended European Search Report from European Patent Application No. 13839358.2, dated Aug. 30, 2016 (8 pages).
(Continued)

*Primary Examiner* — J M Saint Surin
(74) *Attorney, Agent, or Firm* — Kagan Binder, PLLC (57) ABSTRACT

The invention relates to a device and a method for remotely determining the impulse response of an object irradiated by a pulse train with low-intensity pulses of electromagnetic radiation. A complete representation of the pulse train transmitted towards the object is known in advance, and a convolution between the signal representation of the pulse train and the signal of the detected response from the object is performed, which provides a signal representation of the impulse response. Said signal representation can then be
(Continued)

used, e.g., to analyze possible defects in the structure of the object.

20 Claims, 7 Drawing Sheets (51) Int. Cl.
  *G01H 9/00* (2006.01)
  *G01N 29/24* (2006.01)
(52) U.S. Cl.
  CPC ............... *G01N 2291/023* (2013.01); *G01N 2291/0289* (2013.01)
(58) Field of Classification Search
  USPC .......................................................... 73/587
  See application file for complete search history.

(56) References Cited

U.S. PATENT DOCUMENTS

| | | | |
|---|---|---|---|
| 6,205,859 B1* | 3/2001 | Kwun | G01N 29/2412 73/579 |
| 2006/0215175 A1 | 9/2006 | Yacoubian | |
| 2007/0015992 A1 | 1/2007 | Filkins et al. | |
| 2010/0037695 A1 | 2/2010 | Tsujita et al. | |
| 2011/0290026 A1 | 12/2011 | Rice et al. | |
| 2015/0366458 A1* | 12/2015 | Kellnberger | A61B 90/39 600/407 |

FOREIGN PATENT DOCUMENTS

| | | | |
|---|---|---|---|
| WO | WO2009103502 | * | 8/2009 |
| WO | WO2013167147 | * | 11/2013 |

OTHER PUBLICATIONS

Lebedew, Peter "Untersuchengen über die Druckkräfte des Lichtes", Annalen der Physik, Jan. 1, 1901, pp. 433-458, Retrieved from the Internet: URL: http://onlinelibrary.wiley.com/doi/10.1002/andp.19013111102/abstract (machine translation of pages noted in Extended European Search Report).

Mansuripur, Masud "Solar Sails, Optical Tweezers, and Other Light-Driven Machines", College of Optical Sciences, The University of Arizona, Proc. of SPIE vol. 8122, No. 1, Sep. 8, 2011, pp. 1-13.

P. Castellini et al., "Measurement of vibrational modal parameters using laser pulse excitation techniques," Measurement 35 (2004) 163-179.

\* cited by examiner

DEVICE AND METHOD FOR REMOTELY DETERMINING THE IMPULSE RESPONSE OF AN OBJECT USING ELECTROMAGNETIC RADIATION

This application claims benefit from International Application No. PCT/SE2013/051105, which was filed on Sep. 23, 2013, which claims priority to Swedish Patent Application No. 1251075-6, which was filed Sep. 24, 2012, the entireties of said patent applications are incorporated herein by reference.

The present invention relates to a device and a method for remotely exciting an object mechanically and subsequently obtaining the mechanical vibration response from the object. More specifically, it relates to a device intended to irradiate an object with electromagnetic radiation in a predetermined pulse sequence in order to subsequently detect the mechanical vibration response from the object.

BACKGROUND

In the field of mechanical testing of materials/(mechanical structural analysis) a method is used where force impulses are applied to the test object using a specially arranged hammer, a so-called mechanical impulse hammer. The impulse hammer is then chosen or arranged with a weight and a striking face generating force impulses whose frequency spectra are appropriate for the specific test. The hammer is further provided with a sensor, which, for each individual stroke, records the time course of the force impulse applied to the object. During the test, using one or more sensors mounted on the object, the vibration response caused by the stroke is recorded. In a subsequent analysis of recorded vibrations and applied force impulse, certain essential mechanical properties of the object can be determined. For example, the method could be used to detect the presence of cracks or other abnormalities in the test object. Additional analysis opportunities can be obtained by replacing the impulse hammer with electromagnetic or piezoacoustic actuators, allowing more arbitrary mechanical excitation forces to be applied to the test object in one or more points. Said test methods, however, require the measuring equipment to be in direct mechanical contact with the test object. In many cases, though, it is desirable to carry out the measurement without contact, at a distance from the test object. Examples of such cases are when the test object has a high temperature, is inaccessible, contaminated or subjected to high voltage. One possibility to perform such contact-free measurement is to use electromagnetic radiation interacting with the object, thereby applying the desired mechanical excitation. In these cases, the required vibration recording may also be performed without contact, for example, using a laser vibrometer.

The basic principle for producing vibrations in objects at a distance using electromagnetic (EM) waves is based on the waves' ability to transfer energy from one point to another, in combination with the ability to convert this energy, in one or more steps, into mechanical vibration energy. The conversion from EM wave into vibration can take place in a number of different ways, and there are a number of more or less well-developed methods to exploit this. For example, mention can be made of a method for generating plasma formation, so-called laser ablation. Here, a material, usually a metal, is illuminated using a pulse of very high intensity. The high intensity of the pulse causes a dielectric breakthrough in the material, which leads to plasma formation with rapid pressure rise, thereby applying a force impulse to the object's surface. Such a method is described in [Kajiwara, Itsuro; Hosoya, Naoki: Vibration testing based on impulse response excited by laser ablation; Journal of Sound and Vibration, 10 Oct. 2011, 330 (21): 5045-5057]. The disadvantage of this approach is, firstly, that the high intensity of the pulse can be directly harmful to the user, and secondly, that the irradiated material is exhausted and destroyed. Furthermore, this comprises a method based on non-linear phenomena which are themselves highly material-dependent—something that greatly complicates the analysis of the response and thus limits the scope of application. Another method known in the art is based on the electrostrictive effect. Here, molecules in the object's surface are polarized in illuminated areas. This gives rise to mechanical stress which can subsequently be read. An obvious disadvantage of this method is that its applicability depends on the polarization characteristics of the material. Most normal structural materials have low electrostrictive effect, which counteracts the general use of the method. In addition, use is sometimes made of a method called the thermoelastic (or thermoacoustic) method, which is based on a relatively brief pulse heating the surface layer of the object, whereupon the thermal expansion of the surface leads to a sudden mechanical deformation of the surface and the most proximate underlying material volume. The duration of the pulse is balanced so that heating occurs as quickly as possible but at the same time so that heating reaches a sufficient depth in order for the heated material volume to cause a sufficient tensile force to deform the underlying structure. The practical design of the method is somewhat similar to that of plasma formation, but with slightly lower, albeit significant, optical effect, which allows for measurements to be non-destructive. It has the potential for relatively high efficiency but requires, as previous methods, extensive optimization with specific design for each measured object and situation. The traceability of the produced mechanical impulse is low and the possibility of controlling the frequency spectrum of the mechanical excitation is insignificant. An example of an analysis of a mechanical component by means of the method is demonstrated in [P. Castellini; G. M. Revel; L. Scalise; Measurement of vibrational modal parameters using laser pulse excitation techniques; Measurement, Volume 25, Issue 2, March 2004, pages 163-179].

SUMMARY OF THE INVENTION

The present invention provides a device and a method according to the independent claims, which overcomes the problems of the prior art by being both non-destructive and effective for hard-to-polarize objects/materials while also providing very good traceability for the applied mechanical impulse. According to the invention, unlike the known methods based on plasma formation or thermal-expansion effect, the momentum of the electromagnetic waves is used, which provides high traceability of the applied force impulse as it is directly proportional to the energy of the electromagnetic wave. Beyond this, it is not necessary for the invention to use high intensities of the pulses. These advantages are achieved by irradiating the object with several pulses over a longer exposure time, whereupon the collective effect of the pulses is calculated. Even when irradiating the object with extremely modest average intensities, in the order of 1-10 W/cm$^2$, the invention provides good results. This is to be compared with the pulsewise intensities of more than $10^{10}$ W/cm$^2$ used in laser ablation. Furthermore, owing to the structure of the pulse train, unlike known methods, the collective force effect generated by the pulse train on the object can be controlled in detail to the desired frequency range. The advantages of the present invention may at least partly be achieved due to the transfer function of the irradiation being linear and time-invariant. Thereby, the irradiation of the object may be avoided to cause any heating of the object.

As only low-intensity pulses are used, it is worth noting that the impact of only one single pulse on the material would be lost in the signal noise from the detection. The highly limited excitation obtained by a low-intensity pulse leads to a mechanical response so limited that it is not detectable using known detection means. This is the reason why high-intensity pulses are used in the prior art; in this case the energy transfer leads to considerable excitation that cuts through the noise and can therefore be easily detected. To obtain the mechanical response, the invention instead uses the fact that a large number of pulses hit the object. This corresponds to a radiation pressure acting on the object, and by extending the exposure time so that it stretches over a large number of pulses, it is possible to use the invention to obtain the mechanical responsive with low-intensity pulses.

Consequently, the present invention, according to the independent claims, provides a device and a method intended to remotely determine the mechanical response from an object. These are both effective and safe, and work for a wide range of materials in the object. The invention also offers the possibility of obtaining an impulse response from an object that is not practically or conveniently reached using direct contact. It can be a matter of faraway objects, objects of high temperature, radioactive objects, high-voltage objects, objects involving safety requirements, for example in mine clearance, and microscopic objects. It may also involve objects from which impulse responses cannot be obtained using the conventional methods, such as plants and liquids. A further opportunity offered by the invention is remotely obtaining impulse responses from chemical or biological sensors, thereby avoiding electrical contact with the sensors. The reading of impulse responses according to the invention can be done for objects up to a couple of hundred meters away from the device. Further, since the present invention may determine the mechanical response from an object without causing any, or at least very low, heating of the object, the device and method according to the present invention may be used with a larger variety of objects. Such objects may be objects too sensitive to the heat, or objects with a surface not suitable for a method with thermal-expansion effect. A method with thermal-expansion effect is for instance not suitable for objects with a highly reflective surface, opposite to the present invention.

Mechanical response or vibration response refers to the detected response from the excited object, as a result of the exposure to electromagnetic radiation. The detected response can be the response in the excited object caused by the momentum of the electromagnetic radiation. Impulse response refers to the result of convolution between a signal representation of the mechanical response and a signal representation of the pulse train of electromagnetic radiation emitted towards the object.

The irradiation of the object and the detection of the mechanical response may take place in substantially the same point or region of the excited object. Alternatively, the irradiation and detection may take place on opposite sides of the object, or at different separated regions of the object. Detection can be performed continuously during the excitation of the object.

According to one embodiment, said device for emitting electromagnetic radiation can comprise a laser for emitting optical radiation. The light can then provide a visual confirmation of where the measurement takes place. Alternatively, with a laser using radiation outside the visible range, a separate pilot laser can be used. A further advantage of using a laser for excitation of the object can be the laser directivity, which can provide an irradiation spot of 1-30 mm. Furthermore, the laser may be advantageous for the excitation of objects made of a material not suitable for the excitation by radar, such as glass or porcelain, which do not interact with radar radiation.

According to one embodiment, said device for emitting electromagnetic radiation can comprise means for emitting radar waves. When there is a need to use long wavelengths in the electromagnetic radiation, radar waves can be used for the irradiation of the object. Furthermore, radar can be advantageous for the excitation of large objects, such as building structures, façades or land areas. Radar also has the advantage that the excitation can penetrate surface layers or coating on an object on which the laser otherwise acts directly. For example, in rain or fog the radar range can be an advantage where the laser may otherwise be obstructed. Radar can also be used to avoid the risk of eye injuries.

According to one embodiment, the pulse train may be arranged to be controlled by a mathematical statistical distribution function. Said distribution function can be a rectangle distribution, a Poisson distribution or a normal distribution. The sequential pattern can specify the temporal occurrence and the width of the pulses in the pulse train. The sequential pattern may be randomly generated.

According to one embodiment, the signal representation of the continuously detected mechanical responses can be stored before convolution is performed. In one embodiment, these signal representations can be stored for a time period corresponding to the length of said pulse train before convolution is performed. Thus, convolution can be performed between the signal representations of the mechanical response and the pulse train, both signal representations representing a uniform duration. The resulting impulse response from the convolution can have a duration different from the length of the signal representations. Detection of the mechanical response may be performed by a detection device, and the convolution may be performed by a signal processing unit. Storage of the signal representation of the detected mechanical response may take place in the detection device. The detection device may include a storage medium for storing said signal representation. When appropriate, the stored signal representation can be transferred to the signal processing unit. This point in time may be after the entire pulse train has excited the object and the corresponding mechanical response has been detected and stored, or on repeated occasions after subsets of the pulse train have excited the object. Alternatively, the signal representation of the mechanical response can be stored in the signal processing unit. Detected signals from the detection device may then be transferred continuously to the signal processing unit for storage and subsequent convolution. The signal processing unit may comprise a storage medium for storing said detected signals. The detection device and the signal processing unit may be arranged for any of the storage options described above. Communication between the detection device and the signal processing unit can take place via an electrical connection, or via a wireless connection.

According to one embodiment, convolution may comprise a calculation using a transfer function that is linear and time-invariant. This could mean that different measurements using a pulse train of the invention in a series of measurements are to produce results with a linear relationship. There are several ways to achieve this; for example, different measurements of a series of measurements may use the same pulse train, but with different intensity. This can be done by the method comprising a repetition of the steps of irradiating an object with a pulse train, detecting the mechanical response and performing a convolution between the detected response and the pulse train. In the new reading, a pulse train can be used that is equal to that of the first reading, with the difference that they have different intensity. The difference in intensity is chosen so as to produce a linear relationship between the intensities, and hence the read impulse responses.

According to one embodiment, the method may comprise a step of dividing the pulse trains and the detected mechanical response into two or more corresponding sub-intervals, which are then convolved to obtain the impulse response for each sub-interval. This may provide a time-invariant method that is independent of the time when convolution takes place within a measurement. An evaluation can be made after the convolution to verify that the corresponding sub-intervals cover the same time span of the transmitted pulse train.

According to one embodiment, the device for emitting electromagnetic radiation can be adapted to irradiate the object with electromagnetic radiation whose momentum causes the mechanical response. The obtained force impulses are linearly dependent on the intensity and produce the least possible heating or other negative impact on the object, which means a high degree of time invariance. This allows the LTI conditions (linear and time-invariant) to be met for the use of the convolution.

According to one embodiment, device or method may use the wavelength and intensity of the electromagnetic radiation to calibrate the radiation such that the transfer function is linear and time-invariant. Such calibration may be made to be suitable for a wide variety of objects. Other properties of the radiation, such as beam shape and size may also be used for calibration of the radiation.

According to an alternative embodiment, the cause of the detected mechanical response may be, for example, thermoacoustic or plasma-forming effects, as these effects have significantly greater mechanical impact on the object than the momentum. This is possible in cases where a model can be devised that can transfer the recorded mechanical response into a linear and time-invariant response, enabling the convolution. The method of the invention may thus in one embodiment comprise a step of devising a model to transfer the detected mechanical response into a linear and time-invariant response.

BRIEF DESCRIPTION OF THE INVENTION

Before a more detailed description of the embodiments is given below, here follows an overall description of the physics behind the device as well as its design and use. FIGS. 1, 2, 3 and 4 will be used for ease of understanding.

Figure 1:
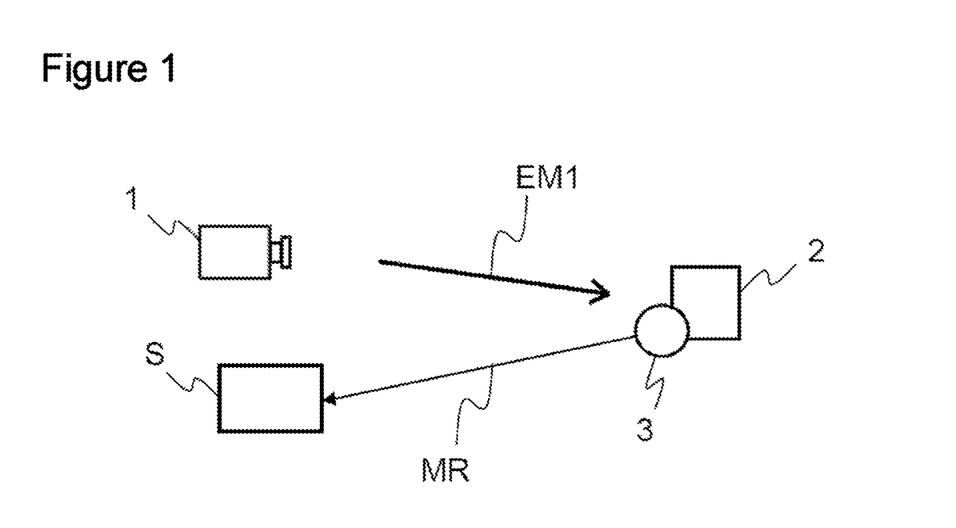
FIG. 1 shows a schematic image of how the vibrations of an object are generated from a distance using pulses of electromagnetic radiation. Further, it is illustrated how the vibration response is detected by a detection device. In the figure, the detection device is shown schematically as a sensor, e.g., an accelerometer.
Figure 2:
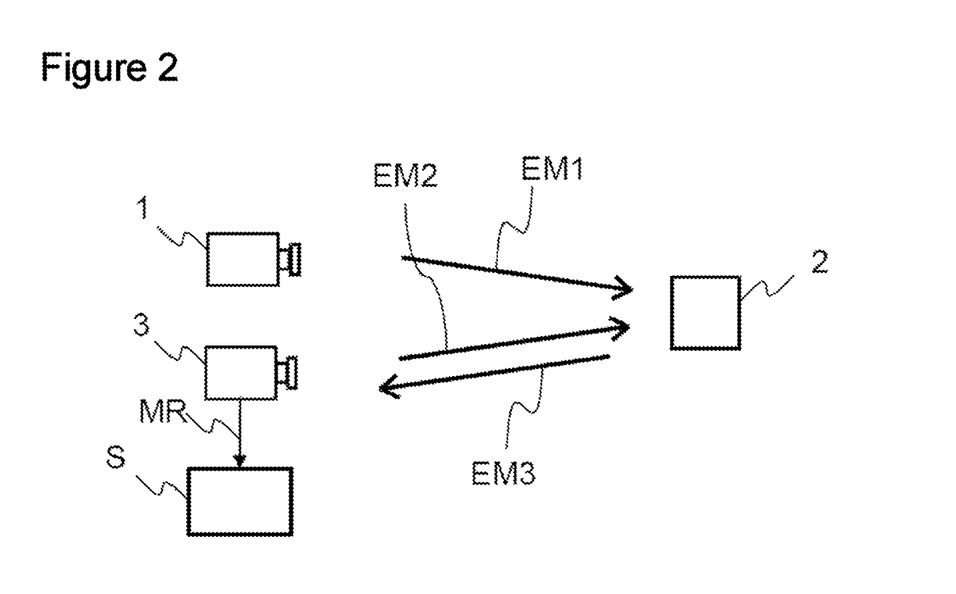
FIG. 2 illustrates the same function as FIG. 1, but here the detection device is shown in the form of a laser vibrometer.

The methods of the prior art mentioned earlier are used, inter alia, to try to determine the mechanical response from the object during irradiation. The present invention also has this purpose, but the methods differ in important respects. According to the present invention, the radiation pressure of the EM waves is used to apply force impulses to the object. The radiation pressure is caused by EM waves interacting with the matter, thus resulting from reflection and absorption. The radiation pressure that can be achieved with reasonable intensities is very low. According to the present invention, the radiation pressure is used to determine the vibration response from both microscopic and macroscopic objects. This is accomplished by irradiating the object with specifically intensity-modulated EM waves in the form of a pulse train consisting of several low-intensity pulses. The irradiation continues over a certain time span during which a continuous detection of the mechanical response takes place. FIGS. 1 and 2 illustrate this schematically. Reference designation (1) refers to a device for emitting EM waves; this device may be comprised of a laser. Reference designation (2) refers to the object being irradiated, and reference designation (3) refers to a detection device for detecting the mechanical response of the object (2). In FIG. 2, the detection device comprises a separate laser using laser vibrometry to obtain the vibration response.

Figure 3:
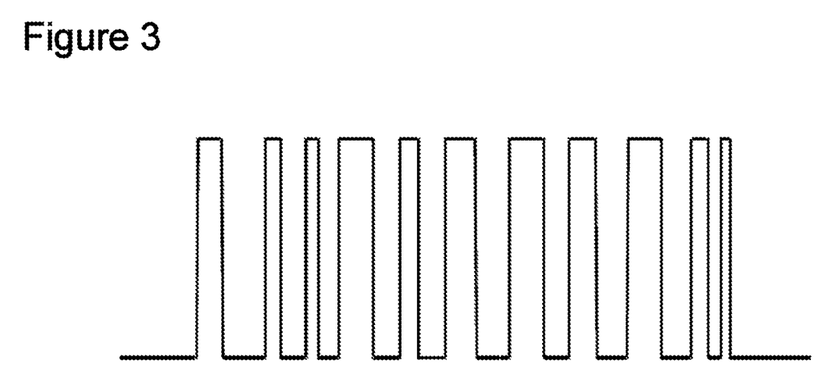
FIG. 3 illustrates how a random sequential pattern that can be used according to the present invention may look.
Figure 4:
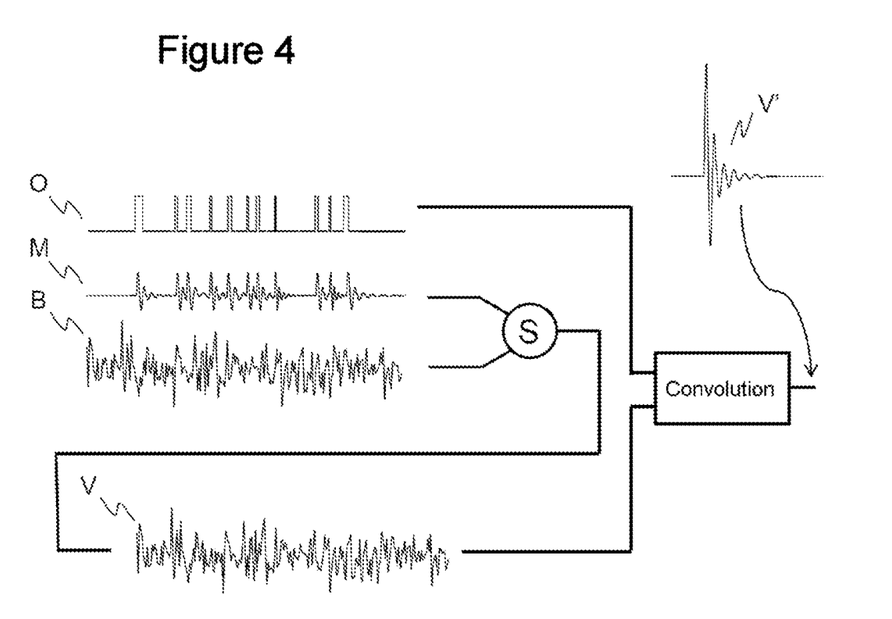
FIG. 4 illustrates schematically how the sequential pattern, the vibration signal and the background noise may appear in the time domain. Further, it is illustrated how the signal representation of the impulse response may look after a convolution.

FIG. 3 shows an example of the appearance of the pulse train, which exhibits a randomly distributed transmission of individual pulses. After some time has elapsed, a convolution is performed between the obtained vibration response signal and the transmitted pulse train. This is schematically illustrated in FIG. 4. In this figure, reference designation (O) refers to the pulse train exciting the object, (M) refers to the mechanical response signal, (B) represents the noise in the signal obtained during vibration detection. Finally, (V) refers to the signal of the detected mechanical vibration response. As shown in the image, (V) comprises a combination of signals (M) and (B); although the figure depicts it as a deliberate summation of the signals, it is rather a result of the noise produced during detection of the response signal (M). Consequently, the convolution step is performed to decode it and obtain the pure mechanical response (M). The figure also shows that this convolution is performed between the transmitted signal (O) and the vibration response (V). After convolution, this yields an impulse response signal which schematically looks like the signal (V') being broken away in the figure.

The convolution operation is performed with the pulse train in reverse chronological order and is expressed in discrete time:

$$V'_n = \sum_{m=-\infty}^{\infty} V_{n-m} O_{-m}$$

It should then be understood that the finite time sequences V and O are padded with a sufficient number of zeros in order for convolution to be performed. Convolution need only be calculated for the indices m where the summation yields a result and for the n's where the impulse response emerges. With the given formula, the impulse response is calculated from n=0 up to a positive index of n where the impulse response has faded to a negligible level. To determine the noise level for V', convolution is calculated in a range of desired length and with n<0.

The procedure finally results in an impulse response according to the invention. The result of the convolution can then be used, for instance, to determine anomalies in the object, such as crack formations and the like. Consequently, the device and method of the present invention provide a way for remotely determining the physical status of the object.

The impulse response (V') obtained by the convolution is, according to the above, a superposition of noise (B) from the detection and the significantly weaker mechanical response signal (M). The convolution thus results in a summation of the total signal noise energy caused by the detector during the measurement's time span. The mechanical response signal (M) is, unlike the noise signal, not stochastic, but deterministically determined by the transmitted pulse train and the mechanical response from the object, given by its transfer function. The convolution therefore produces an amplitude summation of the mechanical effect of the individual pulses. An increased number of pulses, corresponding to a longer time span, leads to an improved signal-to-noise ratio. For example, if the exposure time is doubled, the noise energy in the convolved result increases by 3 dB, but the energy of the mechanical response signal increases by 6 dB. The time interval required to achieve the desired signal-to-noise ratio is determined by the application, and depends essentially on the average power of the pulse train, the detector's noise level, and the object's reflectance, absorption and mechanical properties.

The exposure time suitable for an object is related to the object's size, weight, structural composition, acoustic damping factor and/or the radiation's interaction with the target area. For example, an exposure time of 1-5 seconds can be suitable for an object weighing about 100 grams, such as a tin can. Furthermore, an exposure time of 60-180 seconds can be suitable for an object weighing about 80 kg, such as an enameled porcelain insulator.

As for the result of the signal processing during convolution, it is of relevance whether the transfer function, using the EM irradiation pulse as input and the object's mechanical response as output, is linear and time-invariant (LTI system). To obtain an optimum result when using the invention, therefore, the invention can be provided with a verification of linearity and time invariance. This can be viewed as a calibration of the device or method in order to adapt it to the given conditions. Such calibration may comprise adapting the wavelength and intensity of the irradiated pulses to achieve a linear and time-invariant transfer function. Further, the size and shape of the irradiation reaching the irradiated object may be calibrated to achieve a linear and time-invariant transfer function. This calibration may be made without the need to have specific properties of the irradiation for a specific object type. By using the momentum in the object with the linear and time-invariant device and method to determine the impulse response of the object, there is no need to calculate specific parameters for each object, opposite to known methods based on ablation or thermal-expansion effects.

One way to comply with linearity as mentioned above could be to use the same pulse train, but with different intensity levels in a measurement series. For example, the relative scale factors of 1, 3, 10, 30, etc. could be used for intensity. In a verification of the measurement series, the linearity of the resulting impulse responses is examined in relation to their respective used intensities. Subsequently, for the system's running operation in the given measurement situation towards the object, the highest intensity found to be linear is selected. The procedure ensures that the share of force effect from the thermoacoustic effect is insignificant in relation to the force effect from the momentum of the EM wave. In a verification of the measurement series, the convolved results, i.e., two or more impulse responses, exhibit scale factors in accordance with those used for the pulse trains. Other variants to meet the linearity requirement are also possible.

Compliance with the time invariance can be checked by performing a measurement with a pulse train whose time span is longer than the longest conceivable one for the application. For example, a 200-second span can be used for an application where the maximum conceivable time span is 120 seconds. In an evaluation before the convolution, the time span used is divided into a manageable number of sub-intervals. During evaluation, a set of new pulse train signals is then created, each one consisting of the signal contents from the selected sub-intervals and with the signal contents positioned temporally immediately after each other. A corresponding set is created in a similar way for the detected response signal. The convolution then takes place between the edited pulse train signals and the detected response signal for the sub-intervals and causes a set of impulse responses. If a 200-second time span for measurements is used, 40 sub-intervals of 5 seconds can be used. The set of new pulse train signals for the convolution can consist of combinations of signal contents from intervals 1; 1 and 2; 1 through 3; and so on up to 1 through 40. In an evaluation after the convolution, it is verified that the noise and signal energy of the convolved result as a function of measuring time corresponds to what was previously described above.

The longest conceivable exposure time in the application according to the above is dimensioned for the desired signal-to-noise ratio of the impulse response and depends mainly on the energy level of the irradiation pulses; the power spectrum of the mechanical excitation; the object's weight, material and structure; the interaction of the object surface with the EM radiation; and the noise added when recording the mechanical vibration response. A first estimate of the required exposure time can be obtained by, given the above parameters, calculating the impulse quantity theoretically added by the EM radiation as a function of exposure time. Subsequently, comparisons can be made of the required impulse quantities within established methodology using a mechanical impulse hammer on the same contemplated object. Alternatively, the longest conceivable exposure time can be determined by testing, using the above calculated estimate as a starting point.

Under certain conditions, when applying the method for compliance with time invariance, it is noted that other factors influence the choice of exposure time, such as:
- An object surface with high optical absorption in combination with materials having a significant thermoacoustic effect. This is despite the fact that the optimum wavelength was chosen for minimum absorption.
- In the case of long exposure times, typically over several minutes, a temperature change in the object may occur. Examples of causes are varying ambient temperature, other irradiation or internal self-heating.

In these cases, the measurement can be performed as a series of sub-measurements, each one having a determined maximum possible exposure time. The results from each of the measurements will contain impulse responses with small individual differences in frequency characteristics due to the object's variation in temperature. By applying known signal processing methods, for example, by identifying and adjusting these differences in the frequency domains of the impulse responses, the adjusted impulse responses can be averaged over a longer period of time than would otherwise be possible in a continuous measurement limited by the requirement for time invariance.

As the above conditions are met for the convolution, the invention provides excellent detection of the impulse response with very high traceability of the momentum added to the object. The added momentum is proportional to the energy of the pulse train, i.e., the product of pulse duration, intensity, and illuminated area.

Although the inventive device and method presented herein are described with reference to the fact that the momentum of the electromagnetic radiation affects the object and generates the mechanical response detected, the invention may equally well be utilized in applications with thermoacoustic methods or plasma-forming methods. However, these methods have a different influence on the object, which has to be taken into account, such as heating of the object, as the power of the electromagnetic radiation is greater. Other computational models may then be required, for example, as regards convolution, pulse train design and time of exposure.

When there is mention of vibration response and mechanical response, what is referred to according to the invention is always a representation of that response. Normally, this representation is comprised of a signal representation, namely the detector storing the vibration response in the form of a signal. According to the invention, a convolution is to be carried out between this stored signal and the signal of the pulse train that was transmitted towards the object. By performing the convolution between the signals, an excellent value for the impulse response is obtained without having to destroy the material.

When the above-mentioned convolution is to be performed between the signal of the vibration response and the signal of the pulse train, it is necessary for the signal processing unit to hold a signal representation of the transmitted pulse train. This means that the signal processing unit has or obtains access to a substantially identical copy of the pulse train transmitted towards the object. This copy is to include information on the intensity as a function of time of the transmitted pulses.

According to the invention, the composition of the pulse train is to be random or pseudo-random, i.e., seemingly random and deterministic, i.e., the pulse train must not exhibit any simple periodicity. For example, the pulses of the pulse train can be generated as results from statistical distribution functions, each one describing the intensity, width and time occurrence of the pulses. The statistical distribution functions may be comprised of well-known mathematical distribution functions such as a rectangle distribution, a Poisson distribution or a normal distribution. It can also be tailored so that the joint force impulse of the pulses yields the desired time function and spectral appearance. It is thus possible to generate pulse trains where the collective force effect of the pulses mimics conventional mechanical impulse hammers. Furthermore, it is possible to create impulses that are difficult or impossible to achieve with mechanical impulse hammers. Variants of such tailored statistical distribution functions can be easily designed by one skilled in the art by applying the present invention. The invention can also mimic the function of an impulse hammer on objects made of materials for which it would not be possible to use a conventional mechanical impulse hammer.

Illustratively, the pulse train of one embodiment can be formed by assigning to the pulses durations that are statistically rectangularly distributed between 30 µs and 1 ms, the idle period between the illumination pulses having the same statistical distribution. The power spectrum of the collective force effect produced by this pulse train will be constant up to 500 Hz, and thereafter dropping by 20 dB/decade up to about 17 kHz. To take advantage of available peak power of the irradiation source and to minimize the exposure time, it is desirable to design the static distribution functions so as to generate pulse trains of a duty factor close to 0.5.

DESCRIPTION OF PREFERRED EMBODIMENTS

One embodiment of the invention consists of a device designed to perform the following steps:
a) Transmitting predetermined pulse sequences of electromagnetic radiation towards an object whose mechanical response to the radiation is to be determined;
b) Detecting, continuously over time, the corresponding mechanical vibration response, and, after a certain time, transferring the signal representation of this response to a signal processing unit coupled to the detector;
c) Performing, in said signal processing unit, a convolution between the pulse train of electromagnetic radiation and the transferred signal representation of the mechanical response in order to obtain thereby a signal representation of an impulse response where the background noise has essentially been eliminated.
d) Saving and transferring said signal representation of the impulse response to an analysis unit for further analysis.
e) After the relevant signal analysis has been performed on the signal representation of the impulse response, transferring the result to a presentation unit coupled to the signal processing unit and/or analysis unit.

Performing the essential steps above requires a device comprising the following functional components with reference to FIG. 1: a device for emitting electromagnetic radiation (1), a detection device (3), a signal processing unit (S) including the function of signal convolution along with further functions such as preferably a modulator function, an analysis function and a presentation unit. Examples of explicit embodiments are given below.

The device for emitting electromagnetic radiation refers, in one embodiment, to a laser; this is suitable primarily for applications where high directivity is desired, which provides opportunities for relatively precise shaping of the light spot on the object even at great distances. The diameter of the illumination spot can be 1-30 mm, typically about 5 mm. The wavelength of the light is typically about 1,550 nm, but may be varied to adapt to the object in question and to user safety. It is possible to use a radar instead of a laser if the interest is in generating electromagnetic radiation of a longer wavelength. For a radar, an irradiation spot may be 1-5 dm, typically about 2 dm. A typical frequency of the radiation from the radar in this application is 1-10 GHz. This may be of interest if the vibration response is to be obtained from a large object such as a piece of land, buildings or the like. Furthermore, it may be advantageous if personal safety is important, when seeking to avoid the risk of eye injury from a laser, or when a long range of operation is necessary, such as in fog or rain, when the laser has certain limitations. Furthermore, the appropriate exposure times are the same, whether laser or radar is used—however dependent on the weight of the object.

As the principle utilizes the momentum of the light to generate power impulses, the irradiated object's reflection, absorption and transmission should also be taken into account when choosing the wavelength range. As reflection and absorption, unlike transmission, both contribute to the generation of force, the wavelength range should be chosen so as to primarily minimize transmission. Further, total reflection yields a doubled force impulse as compared to total absorption, which is why high reflection is also a priority when choosing the wavelength range. The purpose of the utilization largely governs the type of electromagnetic radiation to be generated, and consequently the generator of said radiation to be used as well. The wavelength may further be chosen for contributing to the transfer function with the electromagnetic radiation as imput and the impulse response of the object being linear and time-invariant.

Detection device refers to any device capable of detecting vibration signals from the object. The detection device may also store the detected vibration signals and transmit the stored information to a signal processing unit. In one embodiment, where the measured object is readily accessible, this can be a sensor such as an accelerometer. In embodiments where direct contact with the object is precluded, a laser vibrometer or a directional microphone can be used.

The function of the laser vibrometer is based on the continuous illumination of the object by a laser beam. The vibration signal is obtained from path length differences between the vibrometer and the measured object. It is important for the laser in the laser vibrometer to emit at a different wavelength than the radiation used to excite the object in question. FIG. 2 schematically illustrates one such embodiment. The laser (1) for irradiating the object (2) emits a beam EM1 with a first wavelength towards the object. The beam EM1 comprises said pulse train (O). The laser of the laser vibrometer (3) emits a beam EM2 with a second wavelength, different from the first wavelength, towards the object. The laser vibrometer (3) receives a reflected beam EM3 from the object (2). The signal representation (MR) of the mechanical response detected by the laser vibrometer is forwarded to the signal processing unit (S).

The signal processing unit (S), which in its simplest form consists of a common personal computer with relevant software, should include functions for the storage of signals, reception of signals and convolution between signals. In one embodiment, it also comprises a function for pulse modulation. Further, in some embodiments, it also needs units for analysis and presentation. Examples of such functions may be a signal-to-audio converter and an audio playback device if the user wishes to listen to the impulse response. In other embodiments, the analysis unit may comprise detection algorithms comparing the impulse response with predetermined signal signatures to determine if there are any differences. In addition to being an audio playback device, the presentation unit may also consist of a display. Which type of presentation unit to use is governed by the use of the device.

The above-mentioned components also have an interconnection, which will now be described with the aid of the drawings. FIG. 1 shows how an electromagnetic radiation device (1), here schematically illustrated as a laser, illuminates an object (2) and how the vibration response is detected by a detection device (3) in the form of an accelerometer disposed adjacent to the object. FIG. 2 instead illustrates an embodiment where the electromagnetic radiation device (1) comprises a laser and the detection device (3) comprises a laser vibrometer. In other embodiments, the detection device (3) may also consist of another type of vibration detector. Also included is a signal processing unit (S) coupled to the laser vibrometer and arranged to receive the detected signal from the laser vibrometer (see step b above).

In order for the device to perform step (a) described above, the appearance of the pulse train transmitted must be modulated according to a predetermined pulse scheme. This can be accomplished by coupling the laser to a pulse modulator controlling the appearance of the transmitted pulses. The predetermined pulse scheme contains all relevant information about the pulses transmitted, i.e., the widths and positions of the pulses. This is necessary to perform the convolution step (step c above) between the detected response signal and the pulse signal. The power and wavelength of the light may also be available in the signal processing unit (S) for the convolution. A more detailed description of how this is achieved and how the modulation can be performed is given below in connection with the description of FIGS. 5a and 5b, and 6a and 6b.

Figure 5A:
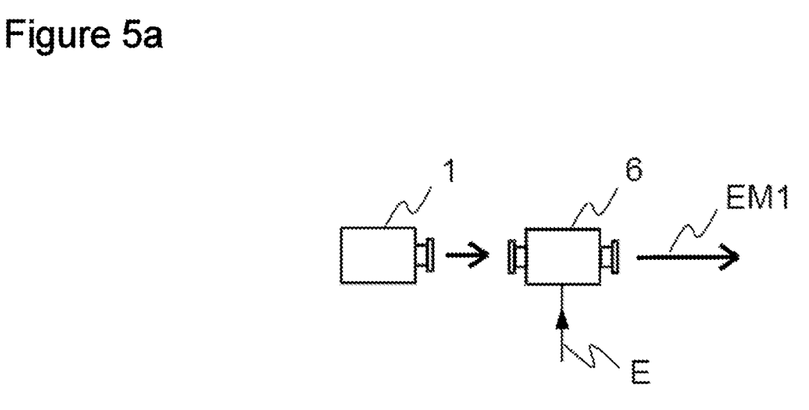
FIGS. 5*a* and 5*b* illustrate two different embodiments for modulation of the pulse trains.
Figure 5B:
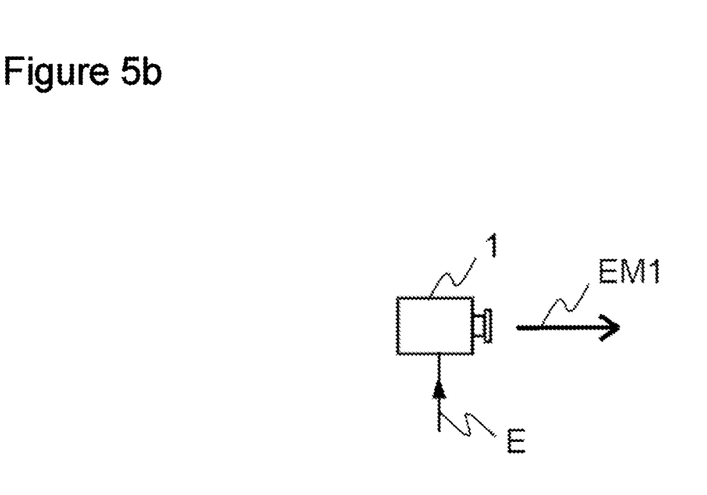

Modulation of the pulse train can be done in a number of different ways. In a first case, contemplated as a normal approach where a semiconductor laser is used, the modulation is integrated into the laser. In its simplest fashion, this is done through the electric drive of the semiconductor laser in combination with a modulating laser actuator. FIG. 5b schematically illustrates one such arrangement. In this figure, the generator (1) of electromagnetic radiation comprises an internal modulator which, by controlling an electrical input (E), yields a pulse train designated by (O). FIG. 5a instead shows schematically how other types of lasers, which cannot be modulated in the same straightforward manner, are advantageously modulated by the insertion of a modulating component (6) into the light path. The modulating component (6) is controlled by an electrical input signal (E). Also here, a pulse train designated by (O) is obtained. Variants of such modulating components well-known in the art may be comprised of:

electromechanical components, such as mechanical shutters, movable mirrors, and the like;
cells with liquid crystals;
components designed to utilize the Kerr effect;
components designed to utilize the Faraday effect.

In addition to the two examples given, using integrated modulation and modulation by means of components in the light path, there are a number of different ways well-known in the art for modulating the pulse trains. How modulation of the pulse train is actually performed is not crucial to the function of the invention; what is crucial is that the modulation can be performed in a controlled manner so that the pulse trains are given a random or pseudo-random distribution.

In operation, therefore, one of the above methods or equivalents is used to transmit a modulated pulse train of laser radiation from the laser.

In order to perform the signal processing steps required to obtain the impulse response, it is assumed that the signal processing unit (S) is in possession of a representation of the pulse train, suitable for the convolution. There are at least two different approaches to provide the signal processing unit with this information. According to the first approach, the pulse train, or pulse trains if several are used can, be fixed and predetermined, albeit without periodicity, thus being storable both in the transmitting unit (1) and the signal processing unit (S). Thereby, the signal processing steps can be performed on the identical copy of the pulse train(s) that is already available. According to the second approach, the representation of the pulse trains is generated and stored only in the pulse transmitting unit (1). They can then be transferred to the signal processing unit (S) continuously or afterwards, when the irradiation of the object (2) has been completed. In this manner, the signal processing unit also obtains an identical copy of the pulse train(s) which can be processed in the signal processing unit intended for the purpose.

Figure 6A:
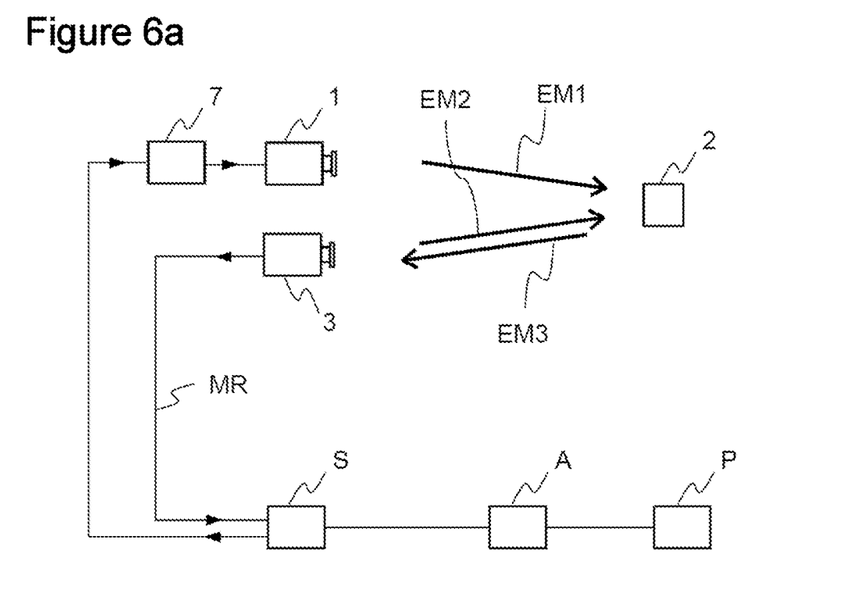
FIGS. 6*a* and 6*b* illustrate, in block form, two variants of the working steps of the device according to two embodiments of the invention.

Reference in greater detail is made to FIG. 6a, which illustrates an inventive device wherein a laser vibrometer is used as the detection device. Here, a predetermined and stored pulse train is used, which is transferred via the signal processing unit (S) to a laser (1) via a laser driver stage (7). The laser (1) transmits the pulse train towards the object (2), and a laser vibrometer (3) detects the vibration response. This vibration response is then transferred to the signal processing unit (S) for convolution. Subsequently, the result of the convolution is transferred to an analysis unit (A) and thereafter to a presentation unit (P). In one embodiment, the analysis unit (A) and the presentation unit (P) can be comprised of the signal processing unit (S).

Figure 6B:
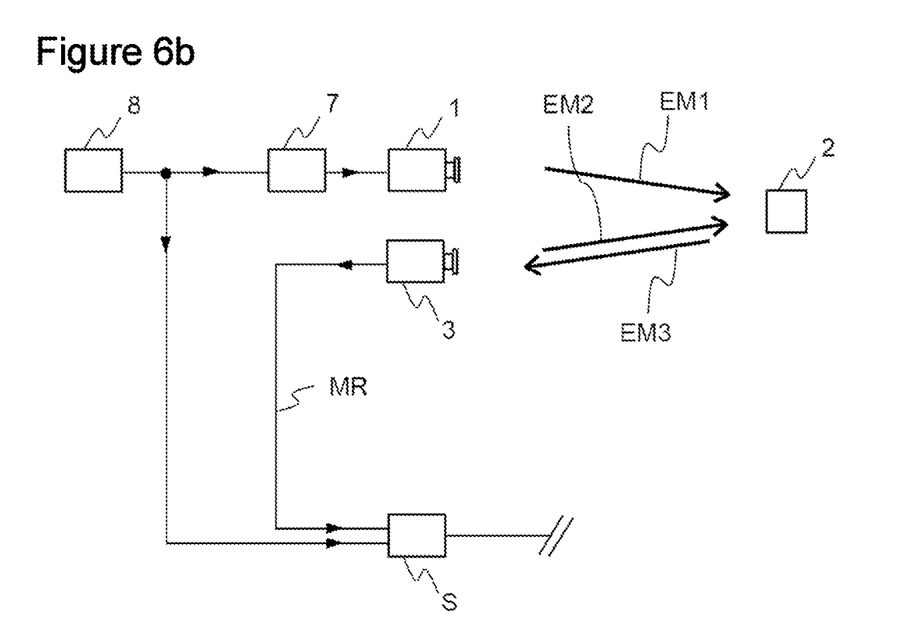

FIG. 6b instead illustrates how the signal representation of the pulse train is simultaneously transferred from a pulse train generator (8) to the laser (1) (via the laser driver stage (7)) as well as to the signal processing unit (S). The laser (1) irradiates the object (2) with the pulse train, and the laser vibrometer (3) detects the mechanical vibration response. Then, the laser vibrometer transfers a signal representation (MR) of the vibration response to the signal processing unit (S), which performs a convolution between the signal obtained from the pulse train generator and the signal obtained from the laser vibrometer. The result (V') of this convolution is then transferred to an analysis unit (A) for further processing. After the analysis has been completed, the response is transferred to a presentation unit (P), not pictured in the drawing. The signal representation transmitted by the pulse train generator can either be transferred continuously to the signal processing unit, or it is also possible for the pulse train generator to store the representation and subsequently transfer the entire signal representation to the signal processing unit after irradiation of the object has been completed.

As previously mentioned, the laser vibrometer (3) works on a wavelength different from that of the laser (1), thereby avoiding interferences. The signal processing unit (S) receives the transferred signal response from the laser vibrometer and stores it for later convolution. After a predetermined time, which can be determined based on the number of transmitted pulses or the elapsed time, the signal processing unit (S) is operable to perform a convolution between the mechanical response signal and the signal representation of the pulse train. This convolution causes a signal representation of the impulse response to be obtained. This signal representation comprises the output from device as well as method. Based on the user's purpose of obtaining the impulse response, the signal processing unit can be equipped with additional functions such as an analysis function and a presentation function. If, for example, the aim is to use sound to determine whether an object has cracks, the analysis unit may consist of a signal-to-audio converter, which converts the signal into an audio file that can be played back by an audio playback device, which here corresponds to the display unit.

Figure 7A:
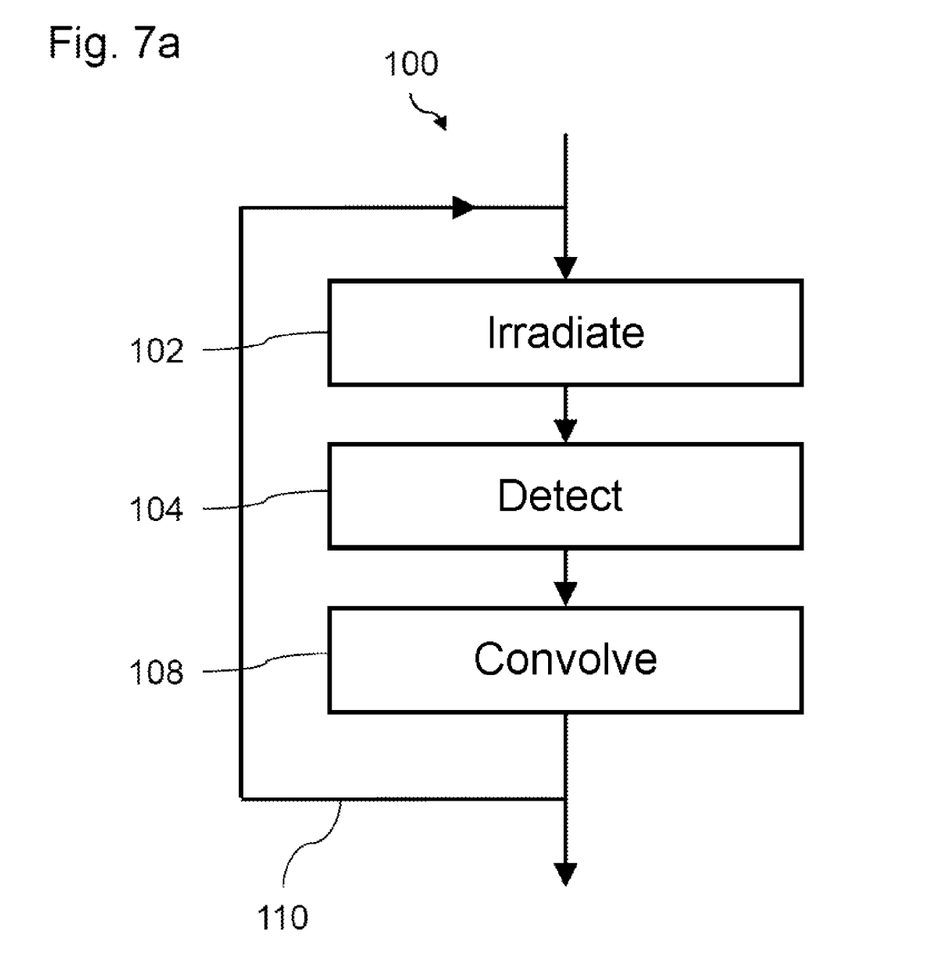
FIG. 7*a* is a flow chart of an embodiment of the invention, providing the steps of obtaining the impulse response from an object excited by electromagnetic radiation.
Figure 7B:
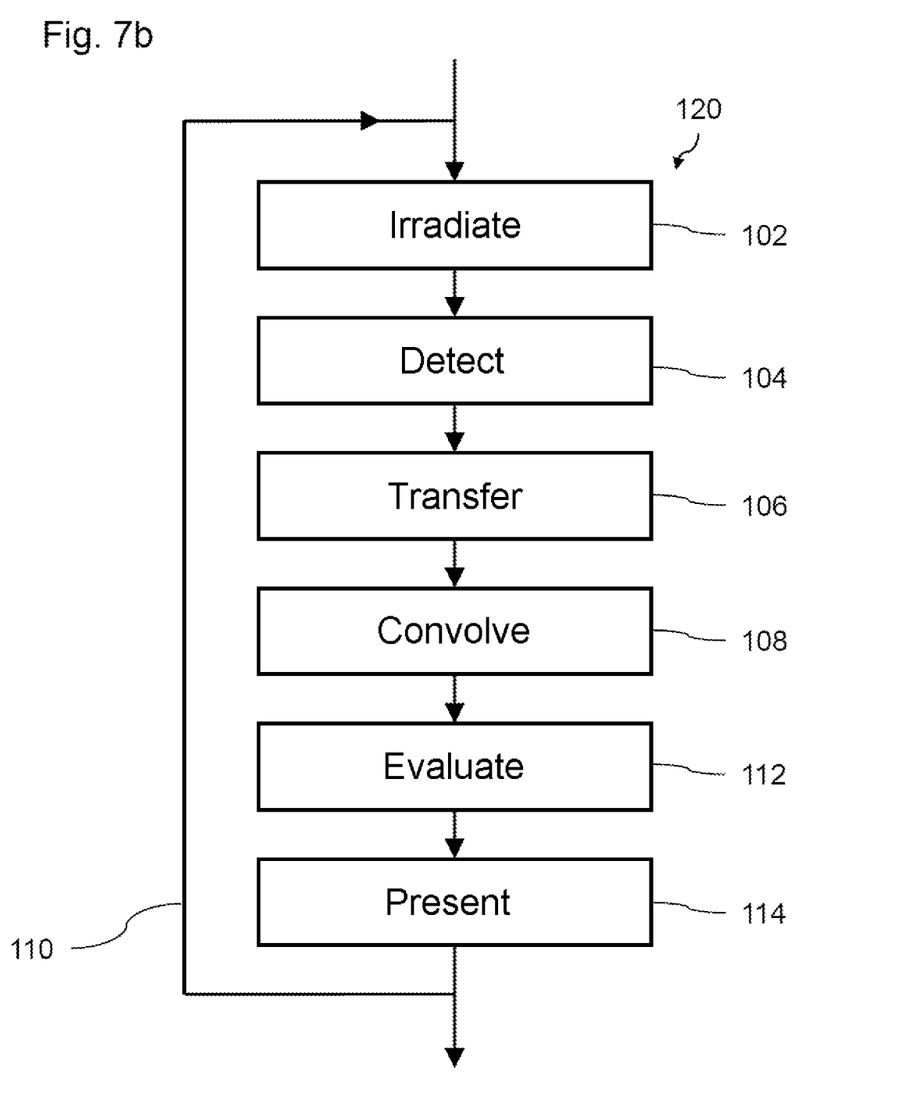
FIG. 7*b* is a flow chart according to an embodiment of the invention, providing the steps of obtaining the impulse response from an object excited by electromagnetic radiation and the steps of evaluating the impulse response and presenting the results to a user.

According to one embodiment of the invention, as shown in FIGS. 7a and 7b, a method (100) is provided for reading an impulse response (V) from an excited object (2). The method includes the steps of irradiating (102) the object (2) with electromagnetic radiation, continuously detecting (104) the mechanical response from the object as a result of the irradiation, and performing a convolution (108) between the signal representation (V) of the mechanical response and a signal representation of the pulse train (O) transmitted towards the object (2). In this way, a signal representation (V) of the impulse response from the excited object (2) is achieved. After convolution (108), a repetition (110) of steps 102, 104, 106 can be performed to make a new measurement, thus reading a new impulse response. A series of measurements can therefore be obtained, comprising a plurality of readings.

FIG. 7b illustrates an extended method (120) for reading an impulse response (V'). As described above, the detection (104) of the mechanical response can be performed by the detection device (3), which can also store a signal representation of the continuously detected mechanical response. At the appropriate time, e.g., after a mechanical response from the entire transmitted pulse train has been detected and stored in the detection device, the stored signal representation can be transferred (106) to a signal processing unit (S) as described above. Alternatively, the transfer can be performed before the storage, which then takes place in the signal processing unit. The signal processing unit (S) can then perform the described convolution. The method (120) can further include a step of evaluating (112) the result from the convolution (108), e.g., performed by the analysis unit (A) described above. The method (120) can also include a step of presenting (114) the result of the convolution (108) and/or of the analysis (112). The presentation may be performed by the presentation unit (P) described above. In the same way as for the method (100) of FIG. 7a, a repetition (110) of the method can be performed to make a new measurement. A series of measurements can therefore be obtained comprising a plurality of measurements.

Applications and Practical Uses of the Present Invention

The device and method of the present invention can be used in all areas of technology where there is a need to precisely determine the vibration response of an object. It may, inter alia, be a matter of determining whether an object has cracks or the like, but it may also be used to remotely determine the hardness of an object, or to identify an unknown object in conjunction with other sensors of a system. The material comprising the object has no significance to the present invention; it can be used for all materials irrespective of hardness. For example, determining the ripeness of berries and fruits from a distance could be contemplated, but equally well identifying defects in building structures.

The invention claimed is:

1. A device for remotely generating and reading the impulse response from an excitation of an object (2), the device comprising:
   a device (1) for emitting electromagnetic radiation;
   a detection device (3) arranged to detect the mechanical response from an object irradiated by the electromagnetic radiation;
   a signal processing unit (S) coupled to said detection device (3) and arranged to receive a signal representation of the response from said detection device;
   wherein said device (1) for emitting electromagnetic radiation is arranged to transmit pulses of a predetermined wavelength and intensity in a pulse train (O) in a predetermined sequential pattern,
   wherein said device (1) is arranged to emit electromagnetic radiation having an intensity that provides that a transfer function with the pulses of electromagnetic radiation from the device (1) as input and the mechanical response of the object detected by the detection device (3) as output is linear and time-invariant,
   and that said signal processing unit (S) is arranged to perform a convolution between a signal representation of said pulse train (O) and a signal representation (V) of said mechanical response (M) and noise (B) detected by the detection device (3) in order to obtain thereby a signal representation (V') of the impulse response from the excited object (2).

2. The device as claimed in claim 1, wherein said device (1) for emitting electromagnetic radiation comprises a laser for emitting optical radiation.

3. The device as claimed in claim 1, wherein said device (1) for emitting electromagnetic radiation comprises a device for emitting radar waves.

4. The device as claimed in claim 1, wherein said detection device (3) comprises an accelerometer.

5. The device as claimed in claim 1, wherein said detection device (3) comprises a laser vibrometer.

6. The device as claimed in claim 1, wherein said predetermined sequential pattern is arranged to be controlled by a mathematical statistical distribution function.

7. The device as claimed in claim 6, wherein said mathematical statistical distribution function comprises a rectangle distribution, a Poisson distribution or a normal distribution.

8. The device as claimed in claim 1, wherein the device further comprises a pulse train generator (8) arranged to generate a signal representation of the pulse train in said sequential pattern to the device (1) for emitting electromagnetic radiation and to the signal processing unit.

9. The device as claimed in claim 1, wherein said detection device is arranged to store the signal representation of the detected mechanical response on a storage medium, and is arranged to transfer the stored signal representation to the signal processing unit at a predetermined time.

10. The device as claimed in claim 1, wherein the device for emitting electromagnetic radiation is arranged to emit electromagnetic radiation whose momentum causes the mechanical response of the excited object.

11. The device as claimed in claim 1, wherein the wavelength and intensity of the pulses from the device (1) for emitting electromagnetic radiation is calibrated such that the transfer function is linear and time-invariant.

12. A method (100) for remotely exciting an object (2) and reading the impulse response from the excited object, the method comprising by the steps of:
   a) irradiating (102) an object with electromagnetic radiation, said radiation being emitted in pulses of a predetermined wavelength and intensity in a pulse train (O) in a predetermined sequential pattern;
   b) choosing intensities of the irradiation (102) such that a transfer function with the pulses of electromagnetic radiation as input and the mechanical response of the object as output is linear and time-invariant,
   c) detecting (104) the mechanical response from the object;
   d) performing a convolution (108) between the signal representation (V) of the mechanical response and a signal representation of the pulse train (O) in order to obtain thereby a signal representation (V') of the impulse response from the excited object (2).

13. The method as claimed in claim 12, wherein said predetermined sequential pattern indicates a temporal presence and width of the pulses of said pulse train (O).

14. The method as claimed in claim 12, wherein the signal representation (V) of the continuously detected mechanical response is stored for a time period corresponding to the length of said pulse train (O) before convolution (108) is performed.

15. The method as claimed in claim 12, wherein the method further comprises the step of generating said sequential pattern based on a mathematical statistical distribution function.

16. The method as claimed in claim 12, wherein the step of performing a convolution (108) comprises calculation using a transfer function that is linear and time-invariant.

17. The method as claimed in claim 16, wherein the method comprises a repetition (110) of steps a) to c) using a pulse train with the same sequential pattern as the previous pulse train (O), but with a different intensity.

18. The method as claimed in claim 16, wherein the method comprises a step, preceding convolution, of dividing the pulse train (O) and the detected mechanical response into two or more corresponding sub-intervals, the convolution being performed between the sub-intervals of the signal representations of the pulse train and the mechanical response.

19. The method as claimed in claim 12, wherein the step of detecting (104) the mechanical response comprises detecting the mechanical response caused in the object by the momentum of the electromagnetic radiation.

20. The method as claimed in claim 12, wherein the step of arranging said irradiation such that the transfer function is linear and time-invariant comprises a step of calibrating the wavelength and intensity of the electromagnetic radiation such that the transfer function is linear and time-invariant.

* * * * *